United States Patent
Scheuch et al.

(10) Patent No.: US 6,463,929 B1
(45) Date of Patent: Oct. 15, 2002

(54) METHOD AND APPARATUS FOR PROVIDING A CONSTANT MEDICINE DOSE FOR AN INHALIC APPLICATION AT LOW INHALIC FLOW

(75) Inventors: Gerhard Scheuch, Gemunden (DE); Knut Sommerer, München (DE)

(73) Assignee: GSF-Forschungszentrum (DE)

(*) Notice: Subject to any disclaimer, the term of this patent is extended or adjusted under 35 U.S.C. 154(b) by 0 days.

(21) Appl. No.: 09/528,152

(22) Filed: Mar. 17, 2000

(30) Foreign Application Priority Data

Mar. 18, 1999 (DE) .......................... 199 12 265

(51) Int. Cl.$^7$ ...................... A61M 15/00; A61M 16/00; B05D 7/14; B65D 83/06
(52) U.S. Cl. ........................ 128/203.15; 128/203.12; 128/203.28; 128/203.23; 128/200.22; 128/205.13; 128/205.17
(58) Field of Search .............. 128/200.23, 203.12, 128/203.15, 203.24, 203.28, 205.13, 205.14, 205.16, 205.17, 200.22, 203.23, 203.29; 604/131, 132, 133; 222/3, 92, 633, 209

(56) References Cited

U.S. PATENT DOCUMENTS

| | | | | |
|---|---|---|---|---|
| 4,790,305 A | * | 12/1988 | Zoltan et al. | 128/200.23 |
| 5,318,016 A | * | 6/1994 | Mecikalski | 128/200.14 |
| 5,511,544 A | * | 4/1996 | McKenna et al. | 128/203.28 |
| 5,702,362 A | * | 12/1997 | Herold et al. | 128/203.15 |
| 6,158,428 A | * | 12/2000 | Mecikalski | 128/200.23 |
| 6,263,873 B1 | * | 7/2001 | Hedenberg | 128/203.12 |

FOREIGN PATENT DOCUMENTS

| | | | | |
|---|---|---|---|---|
| GB | 2182249 A | | 5/1997 | .......... A61M/11/00 |
| WO | WO 93/25258 | * | 12/1993 | |

OTHER PUBLICATIONS

European Search Report for Application EP00105665, Mar. 20, 2001.

* cited by examiner

*Primary Examiner*—Dennis Ruhl
*Assistant Examiner*—Darwin P. Erezo
(74) *Attorney, Agent, or Firm*—Myers Bigel Sibley & Sajovec

(57) ABSTRACT

In a method of and a device for providing a predetermined constant medicament dose for an inhalational administration at a low inhalation flow rate, a closed container 11 is provided which is reducible in terms of volume and comprises a mouthpiece 12 for receiving a predetermined volume of a quantity of medicated aerosol, which is preferably inhalable in one breath, wherein the container 11 is compressed under air-flow control in a direction towards the mouthpiece 12 for preparation of the filling operation, subsequently a means for powder aerosol production is connected to the mouthpiece 12, and finally the container is filled at a high flow rate by air-flow controlled expansion of the container for the introduction of air through the powder aerosol generator.

30 Claims, 1 Drawing Sheet

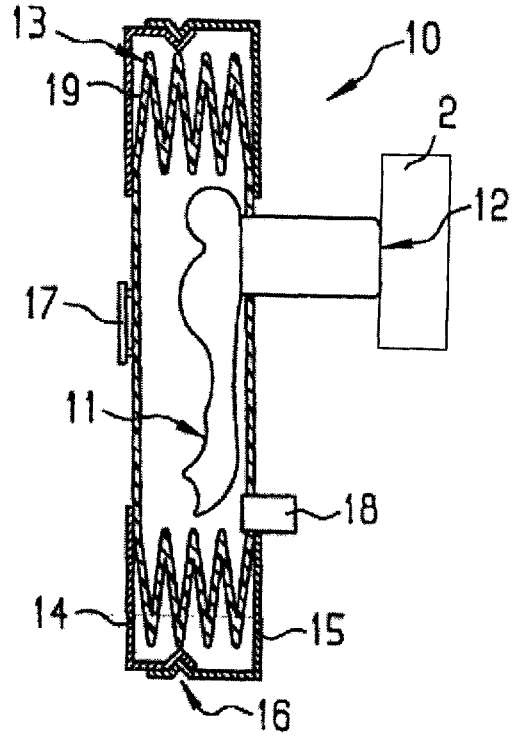
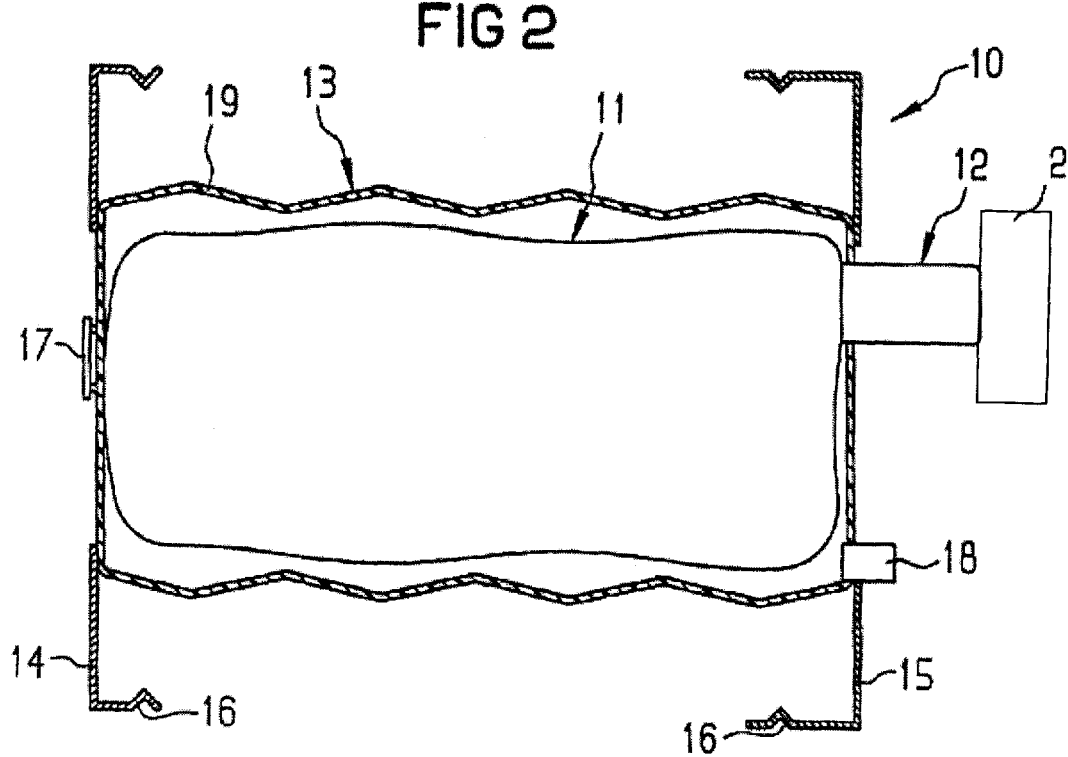

METHOD AND APPARATUS FOR PROVIDING A CONSTANT MEDICINE DOSE FOR AN INHALIC APPLICATION AT LOW INHALIC FLOW

RELATED APPLICATION

This application relates to German patent application no. 199 12 265.2, filed Mar. 18, 1999, the disclosure of which is hereby incorporated herein by reference in its entirety.

FIELD OF THE INVENTION

The present invention relates to a method of providing a constant medicament dose for an inhalational administration at a low inhalation flow rate, as well as to a device appropriate to this end.

BACKGROUND OF THE INVENTIONS

The inhalation of medicaments is gaining an ever-increasing importance. In this respect firstly attention must be paid to the fact that aerosol particles efficiently arrive in the lung only wit slow inhalation, i. e. at a low inhalation flow rate. With the so-called powder inhalers so far known, however, comparatively high inhalational flow rates in the range of roughly 60 1/m are required in order to supply to the powder the necessary energy for the creation of inhalable particles by disagglomeration. This aerosolisation of powders is, however, not or only insufficiently possible for the majority of patients because they are not able to inhale at such a high flow rate. To this adds that a high aerosol flow rate is inexpedient for the inhalational administration of medicaments because with such an application a substantial portion is deposited in the oropharyngeal cavity, particularly in the glottis, rather than arriving in the lungs.

Another problem involved in the inhalational administration of medicaments consists in the fact that the patients vary the volumes of inspiration, which gives also rise to a substantial variation of the medicament doses arriving in the lung. Such a variation of the volume of respiration occurs not only on one patient but is also subject to variations from patient to patient.

There is accordingly a strong need to provide a constant medicament dosage for inhalational administration at a low inhalation flow rate in order to achieve a selective effect depending on the site of application and the administered dose for the medicaments to be applied.

SUMMARY OF THE INVENTION

In accordance with the present invention this need is satisfied by a method of the type outlined by way of introduction, which consists of the steps of method defined in Patent Claim 1. In terms of the device a solution is provided by the features defined in Patent Claim 6.

Preferred further embodiments of the method or the device, respectively, can be derived from the respective dependent patent claims.

In the inventive method hence the provision of a closed container with mouthpiece is defined, which can be reduced in terms of volume and which receives a predetermined volume of a medicated aerosol quantity to be preferably inhaled in one breath, the compression of the elastic container in a direction towards the mouthpiece, the connection of a means for powder aerosol production to the mouthpiece, and the flow-controlled expansion of the elastic container for introducing air through the powder aerosol generator means for the purpose of producing the desired aerosol inside the container. The elastic container is surrounded by a closed compressible housing including an inlet valve for expansion and an outlet valve for a flow-throttled discharge of the preferably resilient container through the mouthpiece led out from the housing, with the container being expanded by application of a suction pressure in the housing.

In correspondence with a preferred embodiment of the invention the suction pressure in the housing is generated by external forces, preferably by at least one expansion spring engaging thereon. In an alternative, the suction pressure in the housing can also be created by the re-shaping elasticity of the housing, which is due to the material and which returns the housing into its uncompressed initial condition.

With the inventive method it is thus possible, with simple means without any additional electronic controller, to achieve a reliable provision of a predetermined constant medicament dose for inhalational administration, with the provided air-flow controlled compression during the inhalation as such contributing to the achievement of an effective slow inhalation.

In terms of the device the invention provides for one embodiment wherein a closed container reducible in terms of volume, a mouthpiece connected to the container, on which a powder aerosol generator can be connected for availability of the aerosol, a housing reducible in terms of volume, which surrounds the container on all sides and from which the mouthpiece is led out in sealed form, and means are provided for controlling the air inlet and outlet into or out from the zone between the container and the housing, with the housing being adapted to be changed from a volume compression condition into an envisaged availability condition for creating the envisaged aerosol volume in the container. On account of the inventive design hence a device is made available which is extraordinarily simple to produce and which is suitable for the inhalation at a small or low aerosol flow rate after separate aerosol production.

The means for air inlet and outlet control comprises two one-way valves which are preferably mounted at different locations with mutually counter-acting effect.

In correspondence with a preferred embodiment of the invention the housing is provided with separate means which may be used for expansion of the housing, with the separate means being preferably formed to include at least one externally engaging compression spring whilst the housing has an approximately cylindrical configuration with folding sections on the edge side.

In an alternative the housing may also consist of a resilient material which returns into its initial shape in the availability condition, instead of or in addition to the separate means.

The container in the housing consists preferably of a resilient material and has preferably a balloon-like shape. According to an improvement of the invention it may be fastened not only in the region of the mouthpiece but also in a region spaced therefrom on the inside of the housing so as to promote the latter's inflation for the purpose of aerosol reception.

According to another expedient embodiment of the invention the housing is transparent at least partly for a check of the filling level of the container. With this provision the patient using the device can visually check the quantity of the filling and the aerosol quantity which is still available in the container during inhalation.

In correspondence with another embodiment of the invention the housing is provided with a releasable means for locking of the volume-compressed position, i. e. the position in which the housing and the container accommodated therein are most largely contracted in a direction towards the mouthpiece. On account of the releasable means, e. g. in the form of a biasing means, this so-called volume-compressed position can be used also for a ready-made condition of the device for selling purposes.

In accordance with the inventive device hence a biased housing is made available which is at least partly transparent and comprises a balloon-like container accommodated therein. Any system for powder aerosol production (DPI: Dry Powder Inhalator) can be easily mounted on the mouthpiece in an air-tight manner. When the housing is released from its volume-compressed position for the envisaged automatically occurring expansion the container, which is equally provided in the housing, unfolds under the effect of the generated subatmospheric pressure, with air being sucked through the powder aerosol inhaler into the balloon-type container for producing the aerosol in the desired dosage. In correspondence with a preferred further embodiment of the invention a so-called impaction separator may be provided in the mouthpiece, which retains aerosol particles of major size which have an aerodynamic diameter greater than 10 μm because these particles cannot be inhaled anyhow.

After availability has been ensured the balloon-like container always contains a constant quantity of a predeterminable aerosol which is determined only by the powder aerosol inhaler, the air-flow controlled expansion of the housing and the design of the impaction separator. The device is extraordinarily simple to handle, even for unskilled persons, and after preparation of the aforedescribed availability the patient must only remove the powder aerosol inhaler from the mouthpiece, place his or her lips on the mouthpiece and discharge the balloon-type container in one breath. On account of the air flow control for the region between the housing and the container, which is implemented by a one-way valve, it is ensured that the patient can breathe only at an adjustable maximum flow rate; and due to this flow rate reduction and the limitation of the volume of the balloon-like container a patient inhales always the same aerosol quantity. A deposition in the extra-thoracic region is expediently minimized because the particles of major size are retained in the system already and because the flow rate is limited.

Due to the inventive embodiment of the method and the device the prerequisites are expediently created for an inhalational administration independently of a possible maximum inhalation flow rate of the individual patient, without any undesirable medicament remaining in the pharyngeal cavity for avoidance of extra-thoracic deposition, whilst it is ensured that the dose is constant because a patent inhales a constant volume and an upwardly limited flow. The device can be produced with extraordinarily small dimensions and at low manufacturing costs, with a compact folded condition being advantageous for distribution and transport. Electronic means are not required and only a small expenditure in terms of material is necessary; moreover, the device is suitable for unproblematic application with all dry powder inhalers so far licensed already.

With the new method and the new device hence a constant medicament dose can be expediently made available for inhalational administration at a low inhalation flow rate, which allows for a safe and reliable dimensioning of the volume for a specified range of application whereas dry powder inhalers so far known, which suffer from the shortcomings described by way of introduction, have been suitable for administration of only 2 to 10% of the active medicament substance in the correct dosage. Thus the inventive method and the inventive device serve at the same time to achieve a distinctly improved utilization of the medicaments as such so that the costs incurred by the treatment of patients over a major period of time are also reduced.

As far as the material of the device is concerned an antistatic material is envisaged for the container, which is permissible for use with medicaments, whereas the choice of materials for the housing is restricted only by the envisaged function on account of the absence of contact with the medicaments.

BRIEF DESCRIPTION OF THE DRAWINGS

The invention will now be described in more details in the following with reference to an embodiment of a device. In the drawing:

FIG. 1 is a schematic view of a device in a folded condition; and

FIG. 2 is a schematic illustration of the device according to FIG. 1 after unfolding in a state in which a constant medicament dose is administered for inhalational administration at a low inhalation flow rate.

DETAILED DESCRIPTION OF THE PREFERRED EMBODIMENTS

FIGS. 1 and 2 are schematic views of a device 10 or providing a constant medicament dose for an inhalational administration at a low inhalational flow rate. The device 10 consists of a closed container 11 in the form of an elastic balloon, adapted to be reduced in terms of volume and connected to a mouthpiece 12. The container 11 is enclosed by a housing 13 which can equally be reduced in terms of volume, from which the mouthpiece 12 is led out in a sealed form. The reference numerals 14 and 15 denote a two-part biasing device with a formation 15 for mutual latching, which is fastened on opposite side sections of the housing 13 and which holds the housing 13 in the volume-reduced state illustrated in FIG. 1. The reference numeral 17 schematically denotes a one-way valve which ensures the escape of air from the region between the container 11 and the housing 13 during expansion of the container 11 whilst the air is prevented from entering through this valve. In terms of its geometric design, the valve 17 is so designed that it will ensure the filling of the balloon-like container 11 at a constant flow rate for the envisaged aerosol production during expansion of the housing 13, which will still be explained in the following.

The valve 18 is equally designed as one-way valve and serves the purpose that air will enter into the cavity between the housing 13 and the container 11 during inhalation but cannot escape through the valve. The valve 18 is provided for the envisaged limitation of the inhalation flow rate by virtue of its geometric design, with provisions being possibly made for adjustability of the valve 18 in a form not illustrated here. The valves 17 and 18 hence provide for an air-flow controlled expansion and compression of the balloon-like container 11 so that, on the one hand, an envisaged medicated aerosol will be made available at a constant flow rate (valve 17) and, on the other hand, the prerequisites are created for an inhalational administration at a low inhalation flow rate through the valve 18.

In the embodiment illustrated in FIGS. 1 and 2 the housing 13 has an approximately cylindrical or square configuration with folding sections 19 on the edge side. For the envisaged expansion of the housing 13 the latter is made of an elastic material tending to re-assume its initial shape and to return into the expansion state shown in FIG. 2. In an alternative moreover at least one externally engaging compression spring may be provided for the desired expansion according to FIG. 2, even though this spring is not shown there.

FIG. 2 illustrates the device according to FIG. 1 in an expanded state of the housing 13 and with an expanded filled balloon-like container 11. The device 10 has assumed this state automatically after release of the biasing device 14–16. In the position shown in FIG. 2 the device is ready for the envisaged inhalational administration of a prescribed specified medicament dose at a low inhalational flow rate.

For the production of this envisaged medicament dose in aerosol form provisions are made such that a conventional powder aerosol inhaler 2 is mounted in a sealed form on the mouthpiece 12 in the position of the device 10 according to FIG. 1. After release of the biasing means 14–16 the housing 13 expands and under the effect of the subatmospheric pressure the balloon-like container 11 equally unfolds, which causes air to be sucked in through the powder aerosol generator 2 for aerosol production while this filling of the balloon-like container 11 is performed at a constantly high flow rate due to the air-flow control function of the valve 17, for instance in the range of 560 l/min, for supply of the necessary energy to the powder of the inhaler so that the "inhalable particles" can be formed by disagglomeration.

After the state shown in FIG. 2 has been reached a patient is only required to remove the powder aerosol generator 2, which had been mounted before on the mouthpiece in a sealed form, and can then apply the aerosol filling in the lung in the desired manner in one breath, which is made available by volume and medicament dose, with the inhalation of a constant low flow rate being ensured on account of the valve 18.

The substances applicable according to the present invention include active agents, medicaments, compounds, compositions or mixtures of substances, which achieve a pharmacological, often advantageous effect. This includes food, food supplements, nutrients, medicaments, vaccines, vitamins and other useful active agents. Furthermore, the substances include all physiologically or pharmacologically active substances which achieve a local or systemic effect in a patient. The active agent which may be supplied includes antibodies, antiviral active agents, anti-epileptics, analgesics, anti-inflammatory agents as well as bronchodilators and may be an organic or inorganic compound, which without limitations also includes medicaments having an effect on the peripheral nervous system, adrenergic receptors, cholinergic receptors, skeletal muscles, cardiovascular system, smooth muscles, blood circulation system, neuronal synapses, endocrine and hormone system, immune system, reproductive system, skeletal system, food supply and excretory system, histamine cascade or central nervous system. For example, suitable active agents may comprise polysaccharides, steroids, hypnotics and sedatives, impulion enhancing agents, tranquillizers, antispasmodic and muscle relaxation agents, anti-Parkinson agents, analgesics, anti-inflammatory agents, anti-microbial agents, anti-malaria agents, hormones including contraceptives, sympathomimetics, polypeptides and proteins eliciting physiological effects, diuretics, substances regulating the fat metabolism, anti-androgenous agents, agents directed against parasites, substances having neoplastic and antineoplastic effects, anti-diabetics, food and food supplements, growth promoting substances, fats, stool regulating substances, electrolytes, vaccines and diagnostics.

The method according to the present invention is particularly suited for inhalative application of the following active agents, but is not limited thereto:

Insulin, calcitonin, erythropoietin (EPO), factor VIII, factor IX, cyclosporin, granulocyte colony stimulating factor (GCSF), alpha-1-proteinase inhibitor, elcatonin, granulocyte macrophage colony stimulating factor (GMCSF), growth hormones, human growth hormone (HGH), growth hormone releasing hormone (GHRH), heparin, low molecular weight heparin (LMWH), interferon alpha, interferon beta, interferon gamma, interleukin-2, luteinizing hormone releasing hormon (LHRH), somatostatin, somatostatin analogues including octreotides, vasopressin analogues, follicle stimulating hormone (FSH), insuline-like growth factor, insulintropin, interleukin-I-receptor antagonist, interleukin-3, interleukin-4, interleukin-6, macrophage colony stimulating factor (M-CSF), nerve growth factor, parathyroid hormone (PTH), thymosin alpha 1, IIb/IIIa-inhibitor, alpha-1-antitrypsin, antibodies against respiratory syncytial virus, cystic fibrosis transmembrane regulator gene (CFTR), deoxyribonuclease (DNAse), bactericides, permeability increasing protein (BPI), anti-CMV antibodies, interleukin-I receptor, retinoic acids, pentamidine, albuterol sulfate, metaproterenol sulfate, beclomethasondiprepionate, triamcinolon acetamide, budesonid acetonide, ipratropium bromide, flunisolide, fluticasone, chromolyn sodium, ergotamin tartrate, and the analogues, agonists and antagonists of the aforementioned substances. Furthermore, active agents may be nucleic acids in the form of pure nucleic acid molecules, viral vectors, associated viral particles, nucleic acids associated with or contained in lipids or a lipid containing material, plasmid DNA or RNA or other contructs of nucleic acids useful for cellular transfection or transformation, particular in cells of the alveolar region of the lung. The active agent may be present in different forms, such as soluble or insoluble, charged or uncharged molecules, components of molecular complexes, or pharmacologically accepted auxiliary agents. The active agent may be composed of naturally occurring molecules or the recombinant production thereof, or the molecules may be analogues of the naturally occurring or recombinantly generated active agents, in which one or more amino acids has been added or deleted. Furthermore, the active agent may contain attenuated life vaccine or destroyed viruses for vaccine use. In the case of the agent insulin, naturally extracted human insulin, recombinant human insulin, insulin extracted from bovine and or porcine sources, recombinant porcine or bovine insulin and mixtures of the aforementioned insulins are included. The insulin may be present in a pure, i.e. in substantially purified form but may also contain extracts as usual in commercial practice. The term "insulin" also comprises insulin analogues in which one or more of the amino acids of naturally occurring or recombinant insulin have been added or deleted.

What is claimed is:

1. A method of providing a predetermined constant medicament dose for an inhalational administration at a low inhalation flow rate, said method comprising the steps of:

providing a closed container reducible in terms of volume and comprising a mouthpiece for receiving a predetermined volume of a quantity of medicated aerosol;

compressing said container in a direction towards said mouthpiece;

connecting a means for powder aerosol production to said mouthpiece; and expanding said container for introducing air through the powder aerosol production means to fill said container with aerosol, wherein said step of expanding is controlled by controlling a flow of air;

wherein an elastic container is provided which is surrounded with a closed compressible housing including a high flow-rate inlet valve for expansion and an outlet valve for discharge of said elastic container at a comparatively lower flow rate through said mouthpiece which is led out of said housing, with said expansion of said elastic container being performed by application of a suction pressure in said housing.

2. A method according to claim 1 wherein said step of compressing is controlled by controlling a second flow of air.

3. A method of providing a predetermined constant medicament dose for an inhalational administration at a low inhalation flow rate, said method comprising the steps of:

providing a closed container reducible in terms of volume and comprising a mouthpiece for receiving a predetermined volume of a quantity of medicated aerosol;

compressing said container in a direction towards said mouthpiece;

connecting a means for powder aerosol production to said mouthpiece; and expanding said container for introducing air through the powder aerosol production means to fill said container with aerosol, wherein said step of expanding is controlled by controlling a flow of air;

wherein an elastic container is provided which is surrounded with a closed compressible housing including a high flow-rate inlet valve for expansion and an outlet valve for discharge of said elastic container at a comparatively lower flow rate through said mouthpiece which is led out of said housing, with said expansion of said elastic container being performed by application of a suction pressure in said housing; and wherein said suction pressure in said housing is generated by forces externally applied on the housing.

4. A method according to claim 3, wherein said suction pressure in said housing is generated by at least one expansion spring engaging thereon.

5. A method according to claim 3, wherein said suction pressure in said housing is generated by the selection of a material which returns resiliently into its original shape.

6. A method according to claim 3 wherein said step of compressing is controlled by controlling a second flow of air.

7. device for providing a predetermined constant medicament dose for an inhalational administration at a low inhalation flow rate, said device comprising:

a closed container reducible in terms of volume;

a mouthpiece connected to said container and adapted for the connection of a powder aerosol inhaler for making an aerosol available;

a housing enclosing said container on all sides and adapted to be reduced in terms of volume, from which said mouthpiece is led out in a sealed manner; and flow control means for controlling the flow of air into and out of a region between said container and said housing;

wherein said housing is adapted to be changed from a volume-reduced condition into an expanded availability condition for filling said container with an aerosol volume.

8. A device according to claim 7, wherein said flow control means comprises one-way valves.

9. A device according to claim 7, wherein said container consists of a resilient material.

10. A device according to claim 7, wherein said container is configured to have a balloon-like shape.

11. A device according to claim 7, wherein said container is fastened to said housing at a location spaced apart from said mouthpiece.

12. A device according to claim 7, wherein said housing is at least partly transparent for a check of a filling level in said container.

13. A device according to claim 7, wherein said housing comprises a releasable means for securing the volume-reduced condition.

14. A device according to claim 7, wherein an impaction separator is arranged in said mouthpiece.

15. A device for providing a predetermined constant medicament dose for an inhalational administration at a low inhalation flow rate, said device comprising:

a closed container reducible in terms of volume;

a mouthpiece connected to said container and adapted for the connection of a powder aerosol inhaler for making an aerosol available;

a housing enclosing said container on all sides and adapted to be reduced in terms of volume, from which said mouthpiece is led out in a sealed manner; and flow control means for controlling the flow of air into and out of a region between said container and said housing;

wherein said housing comprises a separate means for its expansion from a volume-reduced condition into an availability condition for filling said container with an aerosol volume.

16. A device according to claim 15, wherein said separate means is designed to comprise at least one externally engaging compression spring.

17. A device according to claim 15, wherein said housing is designed to have an approximately cylindrical or square shape with folding sections on the edge side.

18. A device according to claim 15, wherein said container (consists of comprises a resilient material.

19. A device according to claim 15, wherein said container is configured to have a balloon-like shape.

20. A device according to claim 15, wherein said container is fastened to said housing at a location spaced apart from said mouthpiece.

21. A device according to claim 15, wherein said housing is at least partly transparent for a check of a filling level in said container.

22. A device according to claim 15, wherein said housing comprises a releasable means for securing the volume-reduced condition.

23. A device according to claim 15, wherein an impaction separator is arranged in said mouthpiece.

24. A device for providing a predetermined constant medicament dose for an inhalational administration at a low inhalation flow rate, said device comprising:

a closed container reducible in terms of volume;

a mouthpiece connected to said container and adapted for the connection of a powder aerosol inhaler for making an aerosol available;

a housing enclosing said container on all sides and adapted to be reduced in terms of volume, from which said mouthpiece is led out in a sealed manner; and flow control means for controlling the flow of air into and out of a region between said container and said housing;

wherein said housing consists of a material adapted to return elastically into its initial shape in an availability condition and is adapted to be expanded from a volume-reduced condition into said availability condition for filling said container with an aerosol volume.

25. A device according to claim 24, wherein said container is configured to have a balloon-like shape.

26. A device according to claim 24, wherein said container is fastened to said housing at a location spaced apart from said mouthpiece.

27. A device according to claim 24, wherein said housing is at least partly transparent for a check of a filling level in said container.

28. A device according to claim 24, wherein said housing comprises a releasable means for securing the volume-reduced condition.

29. A device according to claim 24, wherein an impaction separator is arranged in said mouthpiece.

30. A method comprising the steps of:
  a) providing a device for providing a predetermined constant medicament dose for an inhalational administration at a low inhalation flow rate, the device comprising:
     a closed container reducible in terms of volume;
     a mouthpiece connected to said container and adapted for the connection of a powder aerosol inhaler for making an aerosol available;
     a housing enclosing said container on all sides and adapted to be reduced in terms of volume, from which the mouthpiece is led out in a sealed manner; and
     flow control means for controlling the flow of air into and out of a region between the container and the housing;
     wherein the housing is adapted to be changed from a volume-reduced condition into an expanded availability condition for filling the container with an aerosol volume; and
  b) using the device for inhalative application of pharmaceutically active substances.

* * * * *

UNITED STATES PATENT AND TRADEMARK OFFICE
CERTIFICATE OF CORRECTION

PATENT NO. : 6,463,929 B1
DATED : October 15, 2002
INVENTOR(S) : Scheuch et al.

It is certified that error appears in the above-identified patent and that said Letters Patent is hereby corrected as shown below:

Column 1,
Line 17, the caption should read -- Background of the Invention --

Column 4,
Line 26, please change "10 of" with -- 10 for --

Column 8,
Line 36, should read
-- 18. A device according to Claim 15, wherein said container comprises a resilient material. --

Signed and Sealed this

Twenty-seventh Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,463,929 B1
DATED : October 15, 2002
INVENTOR(S) : Scheuch et al.

It is certified that error appears in the above-identified patent and that said Letters Patent is hereby corrected as shown below:

Column 4,
Line 39, should read -- illustrated in FIG. 1. The reference numeral 18 schemati- --.
Line 44, should read -- geometric design, the valve 18 is so designed that it will --.
Line 49, should read -- The valve 17 is equally designed as one-way valve and --.
Line 52, should read -- cannot escape through the valve 17. The valve 17 is provided --.
Lines 55-56, should read -- bly made for adjustability of of the valve 17 in a form not illustrated here. The Valves 18 and 17 hence provide for an --.
Line 60, should read -- constant flow rate (valve 18) and, on the other hand, the --.
Line 62, should read -- a low inhalation flow rate through the valve 17. --.

Column 5,
Line 22, should read -- flow rate due to the air-flow control function of the valve 18, --.
Line 33, should read -- 17. --.

Signed and Sealed this

Twenty-seventh Day of September, 2005

JON W. DUDAS
*Director of the United States Patent and Trademark Office*